(12) United States Patent
Albert et al.

(10) Patent No.: US 7,888,106 B2
(45) Date of Patent: Feb. 15, 2011

(54) MICROARRAYS AND METHOD FOR RUNNING HYBRIDIZATION REACTION FOR MULTIPLE SAMPLES ON A SINGLE MICROARRAY

(75) Inventors: Thomas Albert, Madison, WI (US); Mark McCormick, Madison, WI (US)

(73) Assignee: Roche Nimblegen, Inc., Wilmington, DE (US)

(*) Notice: Subject to any disclaimer, the term of this patent is extended or adjusted under 35 U.S.C. 154(b) by 579 days.

(21) Appl. No.: 10/444,307

(22) Filed: May 23, 2003

(65) Prior Publication Data

US 2004/0009520 A1 Jan. 15, 2004

Related U.S. Application Data

(60) Provisional application No. 60/383,559, filed on May 24, 2002.

(51) Int. Cl.
| | |
|---|---|
| C12M 1/34 | (2006.01) |
| C12M 3/00 | (2006.01) |
| C12Q 1/68 | (2006.01) |
| G01N 33/53 | (2006.01) |
| C07H 21/02 | (2006.01) |
| C07H 21/04 | (2006.01) |

(52) U.S. Cl. ............... 435/287.1; 435/283.1; 435/6; 435/7.1; 977/789; 977/792

(58) Field of Classification Search ............... None
See application file for complete search history.

(56) References Cited

U.S. PATENT DOCUMENTS

| | | | |
|---|---|---|---|
| 5,874,219 A | 2/1999 | Rava et al. | |
| 6,083,763 A * | 7/2000 | Balch | 435/6 |
| 6,232,066 B1 | 5/2001 | Felder | |
| 6,300,063 B1 | 10/2001 | Lipshutz et al. | |
| 6,699,665 B1 * | 3/2004 | Kim et al. | 506/13 |

* cited by examiner

*Primary Examiner*—Teresa E Strzelecka
(74) *Attorney, Agent, or Firm*—Quarles & Brady LLP

(57) ABSTRACT

The present invention provides a microarray for multiple sample analysis that does not require an alignment of well walls with corresponding probe sets. Methods for building and using such a microarray are also within the scope of the present invention.

12 Claims, 1 Drawing Sheet

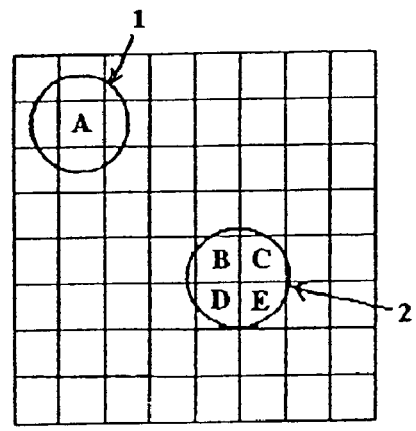
FIG 1
FIG 2
| 1-1 | 2-2 | 3-3 | 4-4 |
| 5-5 | 6-6 | 7-7 | 8-8 |
| 9- | 10-9 | 11-10 | 12-a |
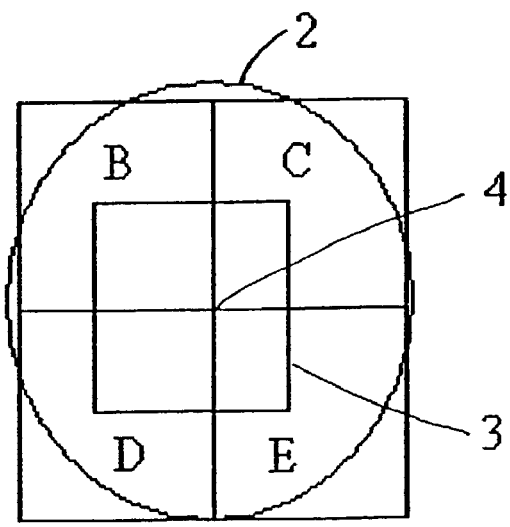
FIG 3

MICROARRAYS AND METHOD FOR RUNNING HYBRIDIZATION REACTION FOR MULTIPLE SAMPLES ON A SINGLE MICROARRAY

CROSS-REFERENCE TO RELATED APPLICATIONS

This application claims priority from U.S. provisional patent application No. 60/383,559 filed May 24, 2002.

STATEMENT REGARDING FEDERALLY SPONSORED RESEARCH OR DEVELOPMENT

Not applicable.

BACKGROUND OF THE INVENTION

The advent of the DNA microarray technology makes it possible to build an array of hundreds of thousands of DNA sequences, or probes, in a very small area, typically a few square centimeters on the surface of a microscopic slide. See, e.g., PCT patent publication Nos. WO 99/42813, 92/10092 and 90/15070, and U.S. Pat. No. 5,143,854, each of which is hereby incorporated by reference in its entirety. A DNA microarray-based assay usually involves hybridizing a DNA or RNA sample to a microarray and scanning the microarray to detect hybridization. The probes in the microarray are organized into areas of similar probes, these areas being referred to as features. By hybridizing experimental DNA or RNA to the probes on the microarray, and detecting in which features the experimental DNA or RNA has hybridized, it becomes possible to obtain much information about the experimental DNA or RNA in a single step relatively simple process. Using this ability, DNA microarray technology has been applied to areas such as gene expression and discovery, mutation detection, allelic and evolutionary sequence comparison, genome mapping, and more.

A state of the art DNA microarray can accommodate hundreds of thousands of features, each containing unique probes. In fact this capacity can exceed the needs of many common useful experiment, many of which involve hybridization assays involving far less probes than a microarray's full capacity. Therefore, some microarrays are constructed in which a set of features are repeated multiple times over the area of the microarray, with each set of features ultimately being exposed to a separate experimental sample, to conduct multiple data collection experiments in parallel. This concept can be thought of as an array of arrays. To do this, it is desirable to make DNA microarrays that can be simultaneously used for multiple samples. To make this work, there must be measures taken to prevent cross-contamination between samples intended for differing areas of the microarray. Currently, the microarrays built for this purpose (e.g., U.S. Pat. No. 5,874,219) use physical wells to separate probe sets for different samples and well walls have to align with corresponding probe sets so that each well contains the correct probes. However, alignment of well walls with corresponding probe sets is not always easy to achieve and a misalignment can lead to inaccurate result.

BRIEF SUMMARY OF THE INVENTION

The present invention provides a microarray for multiple sample analysis that does not require an alignment of well walls with corresponding probe sets. This is achieved by providing a microarray that contains continuous and identical detection blocks (each detection block contains a set of probes of interest) and a signal for identifying a corner point where any four adjacent detection blocks connect. In addition, each well used to separate probes on the microarray is slightly larger than a detection block in all dimensions. With such an arrangement, even if well walls do not align with the detection blocks, each well still contains all the probes of a complete detection block and the identity of the probes in a well can be determined by referring to a corner point also contained in the well.

The microarray of the present invention is not limited by the type of molecules on the microarray. For example, the microarray can be a polynucleotide microarray, a polypeptide microarray or a microarray of other types of molecules. Methods for building and using the microarrays of the present invention are also within the scope of the invention.

BRIEF DESCRIPTION OF THE SEVERAL VIEWS OF THE DRAWINGS

FIG. 1 depicts one microarray embodiment of the present invention that contains continuous and identical detection blocks.

FIG. 2 shows an example of a detection block from the microarray in FIG. 1.

FIG. 3 illustrates how information from a complete detection block is pieced together.

DETAILED DESCRIPTION OF THE INVENTION

The intention of the present invention is to overcome the problem of aligning physical barriers, such as wells, with areas of a microarray, so as to facilitate the use of a microarray to perform multiple parallel hybridization procedures on a single microarray. In fact, the idea of the present invention is to forego entirely any attempt to align physical barriers, such as wells, with the features or areas of features on the microarray. Instead, the wells or barriers are placed on the microarray without any pre-determined alignment. Just by selecting a proper well size in relation to the size of the microarray areas, one can be sure that the needed data can be collected. The concept behind this invention is that the relationship of the barriers or wells to the areas of features is determined after the hybridization data is collected, by analysis of the hybridization data, rather than trying to physically align the wells with the microarray before the experiment. This technique can be thought of as an alignment done in software with the data from the hybridization rather than an alignment done physically before the hybridization.

To understand this concept, the introduction of some terminology is helpful. Again, a feature is a physical area on the microarray in which a number of nucleic acid probes of similar sequence are all anchored. For the purpose of the present invention, a detection block is an area on a microarray slide that contains one complete set of the features of interest that are to be probed with the experimental sample. Thus if the experiment is to use 64 features (an 8 by 8 set of features), the detection block would mean one of the 8 by 8 feature areas containing a complete set of the 64 features of interest. The size of a detection block can be any number of features such that there can be more than one detection block on a microarray. By "continuous detection blocks," we mean that the detection blocks adjacent to each other share borders. The idea behind this concept is that the detection blocks are fabricated on the microarray in repeating units next to each other, such that the detection blocks map over the microarray. If the detection blocks are square or rectangular, each detection block and three adjacent detection blocks share a vertex at each corner of the detection block. This vertex is here referred to as a corner. By "identical detection blocks," we mean that the probes in the features of interest in each detection block are identical in identity and arrangement. It should be noted that the term "identical blocks" are defined with regard to the probes of interest for an assay. For example, two detection blocks that contain different probes that are not of interest for a particular assay at corresponding positions will be considered as identical blocks if they otherwise qualify as identical blocks. A detection block may also contain blank positions (a position available for a probe but is left with no probe). A detection block may also contain features designated for control or features designated for fiducial alignment purposes. An detection block can contain any desired number of features, so long as it can be repeated in the area of the microarray. The detection block need not be square or rectangular, but could be any geometry that lends itself to both arrangement on the microarray and detection of the fiducial boundaries as envisioned here.

Using the technique described here, ultimately set of features on a microarray of the present invention are compartmentalized by physical barriers from other features. A compartment so formed is also called a well. Each well is at least slightly larger than a detection block in all dimensions and is not in fluid communication with other wells during the hybridization process, so that hybridization reaction in one well does not interfere with that in another. The exact way the probes are compartmentalized is not critical for the present invention. For the purpose of the present invention, the shape of each well does not matter and can be uniform or varying. The closer the shape of a well is to the shape of a detection block, the more wells can be formed on a given slide.

As mentioned earlier, an advantage of the microarray provided by the present invention is that the physical barriers do not have to be physically aligned with detection blocks. No matter where a well is located on a microarray, as long as the well is slightly larger than a detection block in all dimensions, it will contain a complete set of features forming a detection block and a corner point where four adjacent detection blocks intersect. Although the relative locations of the complete set of features in the well may be different from that in another well, the identity of the features and the position of the detection block in the well can always be determined by locating first the corner point contained in the well. As long as the detection block are formed in a continuous grid on the microarray, and as long as the well is sufficiently larger than the detection block, the area inside of the well will inevitable contain at least one corner where four detection blocks meet. The idea here is that in order to create a complete data set for the sample in each well, the detection block is created by assemble an complete data set of features from the features that surround a corner. Thus for the data collection purposes, a virtual detection block of features is created from the feature surround the corner rather using the physical detection block designed when laying out the microarray.

The corner is thus detected when the output of the hybridization step is read, typically by fluorescent scanning. There are many techniques by which a corner point can be identified, and one can use any of them for the present invention. For example, one or more positive control probes can be printed onto features arranged on a microarray to identify a corner point. One easy way is to arrange control or fiducial features to a physical cross formation, using the positive control probes, such that the cross intersection coincides with the corner point. One can readily envision any number of other variations using combinations of negative and positive controls that could be used to create a visible pattern that could be used to identify a corner.

Once the corner is detected, the rest of the hybridization data can be rearranged to create complete set of data for a detection block by using the data from the features which surround the corner. The location of each feature relative to the corner can be used to identify which probes are in which features. One can think of this process are re-arranging the location of the features in software to reassemble an entire detection block.

The present invention is most useful for an application in which a hybridization assay is used to analyze a large number of samples with the same relatively small number of probes. Described below is a preferred microarray embodiment of the present invention for such an application.

In this embodiment as illustrated in FIG. 1, the microarray contains 64 identical blocks labeled as block A, B, C, D, E and so on. Circles 1 and 2 represent two wells on the microarray (FIG. 1). FIG. 2 is an example of what one of the identical detection blocks looks like. In this simplified example, there are 12 available feature positions in the block and the number of features of interest from which data is sought in the hybridization assay is 10, leaving two features for controls or fiducials. The first number in each number set shown in FIG. 2 defines feature position of the block and the second number defines a number assigned to each probe. The 10 probes of interest are labeled as probe 1-10 are located at feature positions 1 to 8, 10 and 11, respectively. The feature at feature position 9 does not have any probes constructed in it, and thus is a blank position or negative control. The feature at feature position 12 contains a probe which is not of interest to the hybridization, but which will hybridize to a nucleotide spiked into the experimental sample, i.e. a positive control. All the repeating detection blocks of the microarray in FIG. 1 have the same arrangement of features at corresponding positions 1 to 12.

FIGS. 1 and 3 illustrate how information in a complete block is reconstructed by taking partial information from adjacent blocks. In FIG. 1, well 1 contains a complete detection block A and thus contains all information from one block. The information from the hybridization in well 1 is read by determining the corner, from the location of the corner understanding that the entire detection block A is in well 1, and then simply reading the data from detection block A.

Well 2, however, does not contain any single whole detection block. However, it does contain the information from a whole block that can be obtained by piecing together information contained in the parts of block B-E that are enclosed in well 2. First, the corner at the intersection of detection blocks B, C, D, and E is located. In this simple example, the corner might be located by looking for a lighted feature (feature position 12 of block B) adjacent to a dark feature (feature 9 of detection block C). From the detection of the corner, a data extraction grid 3 of the same size as a detection block can be envisioned inside well 2 (FIG. 3). The grid is placed in such a way so that a corner point 4 where the four blocks connect to each other is included in the grid. The data from all of the features in the grid can be then read and assembled into a data set representing on detection block.

The methodology used for detecting the corner in this simple example is trivial and subject to ambiguity, since there will likely be other instances of a lighted feature next to a dark feature in the data set. This example was just to illustrate the principle. In actual practice, the number of features in the data set and the construction of controls or fiducials can be as elaborate as necessary to allow for the unambiguous detection of corners. Note also that since some of the features will appear multiple times in a well, that redundant reading and comparison of the other features, even features outside of the grid 3, can be used to confirm that the corner has been found and that the detection block is being read correctly.

In view of the microarrays and methods for piecing together information described above, it is well within the capability of one of ordinary skill in the art to build a microarray of the present invention and use it to analyze multiple samples.

It is understood that examples and embodiments of the present invention set forth in the specification are illustrative and not intended to confine the invention. The invention embraces all modified forms of the examples and embodiments as come within the scope of the following claims.

We claim:

1. A microarray comprising:
   a microarray substrate comprising a plurality of identical physical detection blocks in repeating units next to each other, each physical detection block comprising an identically arranged complete set of probe-containing features;
   at least one signal for unambiguously identifying a corner of the physical detection blocks, each feature having an ascertainable position relative to the at least one signal; and
   physical barriers defining on the substrate at least first and second compartments having a shape and being larger than a physical detection block, each compartment defining a virtual detection block comprising at least one of each probe-containing feature, the features in each compartment being members of at least two sets of features, and comprising the at least one signal, the compartments not being in fluid communication with one another.

2. The microarray of claim 1, wherein the probes are polynucleotides.

3. The microarray of claim 1, wherein the probes are polypeptides.

4. The microarray of claim 1, wherein the compartments have the same shape.

5. The microarray of claim 1, wherein the shape is selected from a rectangle, a hexagon and a circle.

6. The microarray of claim 1, wherein the physical barriers can be separated from the microarray.

7. The microarray of claim 1, wherein the plurality of physical detection blocks is at least 4 blocks.

8. The microarray of claim 1, wherein the plurality of physical detection blocks is at least 10 blocks.

9. A method for building the microarray of claim 1 comprising the steps of:
   providing a microarray substrate comprising a plurality of identical physical detection blocks in repeating units next to each other, each physical detection block comprising an identically arranged complete set of probe-containing features;
   at least one signal for unambiguously identifying a corner of the physical detection blocks, each feature having an ascertainable position relative to the at least one signal; and
   positioning physical barriers on the substrate to define first and second compartments having a shape and being larger than a detection block, each compartment defining a virtual detection block comprising at least one of each probe-containing feature, the features in each compartment being members of at least two sets of features, and comprising the at least one signal, the compartments not being in fluid communication with one another.

10. A method of conducting multiple hybridization experiments in parallel on a single microarray, the method comprising the steps of
    providing a microarray according to claim 1;
    physically placing a set of wells on the microarray without aligning the wells to the detection blocks, the wells each being larger in area than a detection block;
    placing different samples in different of the wells;
    performing a hybridization experiment;
    obtaining the data from the hybridization experiment;
    from the data from the hybridization experiment, determining where the corner of a detection block from the data for a well is, and combining the data from features near that corner to reconstruct the data from an entire detection block.

11. The method of claim 10 wherein each detection block includes control features adjacent the corners thereof to assist in locating the corner of each block.

12. A method for running a plurality of hybridization reactions for a plurality of samples on a single microarray, the method comprising the steps of:
    providing a microarray according to claim 4;
    hybridizing one sample to probes in one detection block; and
    hybridizing another sample to probes in another detection block.

* * * * *